DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JUNE 5, 1973

911 O.G. 9

T911,009

METHOD FOR INCREASING THE AVAILABILITY OF DRUGS HAVING HIGH SERUM PROTEIN BOUND CHARACTERISTICS

John H. Perrin, Madison, Wis., assignor to the United States of America as represented by the Secretary, Department of Health, Education, and Welfare

Continuation of abandoned application Ser. No. 93,473, Nov. 27, 1970. This application Sept. 25, 1972, Ser. No. 292,248

Int. Cl. A61k *27/00*

U.S. Cl. 424—317

No Drawing. 8 Pages Specification

A method for improving the availability of highly serum protein bound drugs by administering such drug in combination with a water soluble salt of trichloroacetic acid.